US00PP30665P3

(12) United States Plant Patent
Farrow

(10) Patent No.: US PP30,665 P3
(45) Date of Patent: Jul. 9, 2019

(54) ***CHAMAECYPARIS* PLANT NAMED 'FARROWCGMS'**

(50) Latin Name: *Chamaecyparis pisifera*
Varietal Denomination: FARROWCGMS

(71) Applicant: Michael Wayne Farrow, Warwick, MD (US)

(72) Inventor: Michael Wayne Farrow, Warwick, MD (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 15/732,453

(22) Filed: Nov. 14, 2017

(65) Prior Publication Data

US 2019/0150341 P1 May 16, 2019

(51) Int. Cl.
*A01H 7/00* (2006.01)

(52) U.S. Cl.
USPC ..... Plt./213

(58) Field of Classification Search
USPC ..... Plt./213

CPC ... A01H 7/00; A01H 5/00; A01H 5/02; A01H 5/04; A01H 6/00
See application file for complete search history.

(56) References Cited

PUBLICATIONS

Spring Meadow Nursery Flowering Shrubs Starter Plants Catalog and Shrub Reference 2017-2018, retrieved on Oct. 11, 2018, retrieved from the Internet at https://springmeadownursery.com/files/resource_files/2017-18_SMN_Catalog_1-50.pdf, pp. 1-9 and 37. (Year: 2017).*
Watson, L., and Dallwitz, M.J. Delta Intkey 2008 onwards. The families of gymnosperms. Version: Oct. 14, 2018. delta-intkey.com, retrieved on Oct. 15, 2018, one page. (Year: 2018).*

* cited by examiner

*Primary Examiner* — June Hwu
(74) *Attorney, Agent, or Firm* — Cassandra Bright

(57) ABSTRACT

A new and distinct *Chamaecyparis* cultivar named 'FARROWCGMS' is disclosed, characterized by yellow, yellow green and green foliage. Plants are full and have a compact, semi-dwarf pyramidal habit. Foliage is arranged in tightly held scales, forming an attractive texture. Plants exhibit rapid growth. Foliage color is maintained throughout Winter. The new cultivar is a *Chamaecyparis*, suitable for ornamental garden purposes.

2 Drawing Sheets

Latin name of the genus and species: *Chamaecyparis pisifera.*

Variety denomination: 'FARROWCGMS'.

BACKGROUND OF THE INVENTION

The new cultivar is a product of chance discovery by the inventor, Michael W. Farrow. This new variety, hereinafter referred to as 'FARROWCGMS', was selected as a naturally occurring branch mutation from the parent *Chamaecyparis pisifera* 'Golden Mop', unpatented. The novel variety was discovered in a commercial nursery in Warwick, Md. during 2010.

After identifying the new variety as a potentially interesting selection, first propagation of 'FARROWCGMS' occurred by softwood cuttings at a commercial nursery in Warwick, Md. in 2012. The inventor continued controlled testing and propagation, assessing stability of the unique characteristics of this variety. Five generations have been reproduced and have shown that the unique features of this cultivar are stable and reproduced true to type.

SUMMARY OF THE INVENTION

The cultivar 'FARROWCGMS' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'FARROWCGMS' These characteristics in combination distinguish 'FARROWCGMS' as a new and distinct *Chamaecyparis* cultivar:

1. Very full plants.
2. Good Summer and Winter color.
3. Attractive foliage texture with tightly held scales.
4. Semi-dwarf plant with a compact, pyramidal shape.
5. Fast growth rate.

COMMERCIAL COMPARISON

'FARROWCGMS' can be compared to the commercial variety *Chamaecyparis pisifera* 'RIKACPMC' application Ser. No. 15/530,102. The varieties are similar in most horticultural characteristics, however, plants of 'FARROWCGMS' differ in the following ways:

1. New cultivar yellow throughout; comparator has yellow tips.
2. New cultivar is more upright growing; comparator grows outward.

PARENTAL COMPARISON

'FARROWCGMS' can be compared to the parent *Chamaecyparis pisifera* 'Golden Mop'. The varieties are similar in most horticultural characteristics, however, plants of 'FARROWCGMS' differ in the following ways:

1. New cultivar is more compact and triangular; parent is shaggier with a more spreading habit.

BRIEF DESCRIPTION OF THE PHOTOGRAPHS

Figure 1:
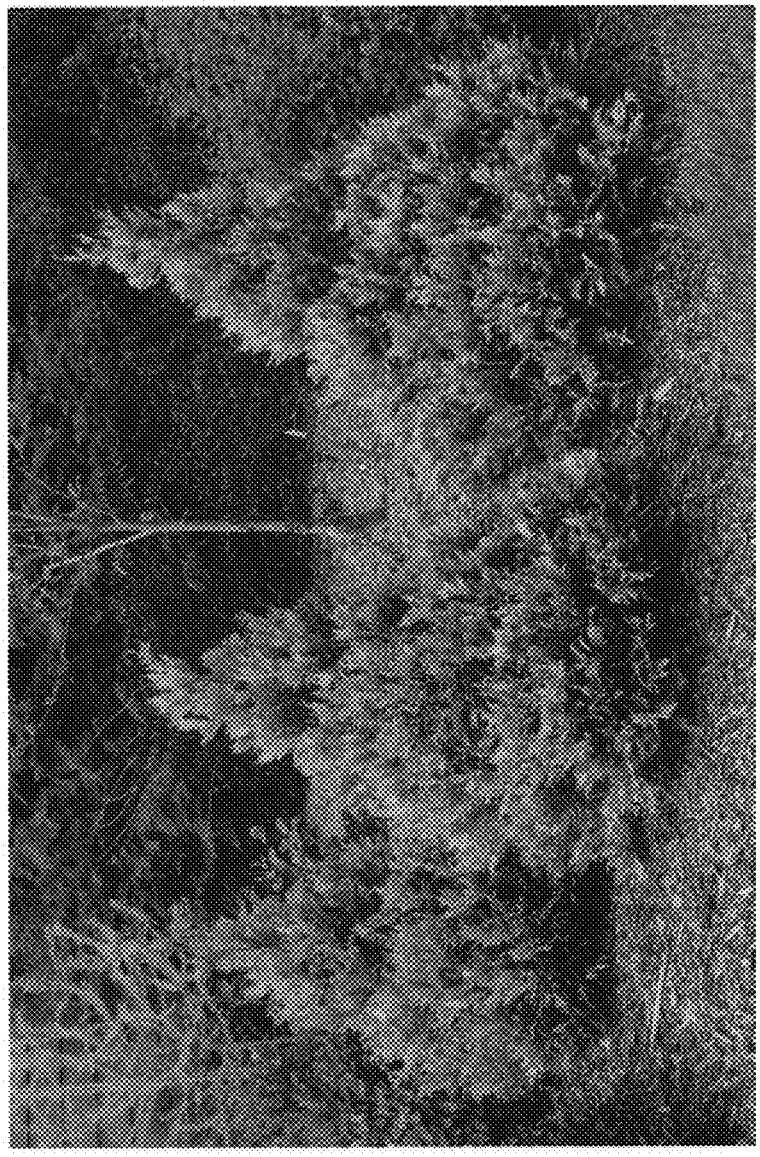

The accompanying photograph in FIG. 1 illustrates in full color a typical plant of 'FARROWCGMS' grown outdoors in Grand Haven, Mich. Plants in FIG. 1 are approximately 5 years old, and exhibit the characteristic full, compact and pyramidal growth.

Figure 2:
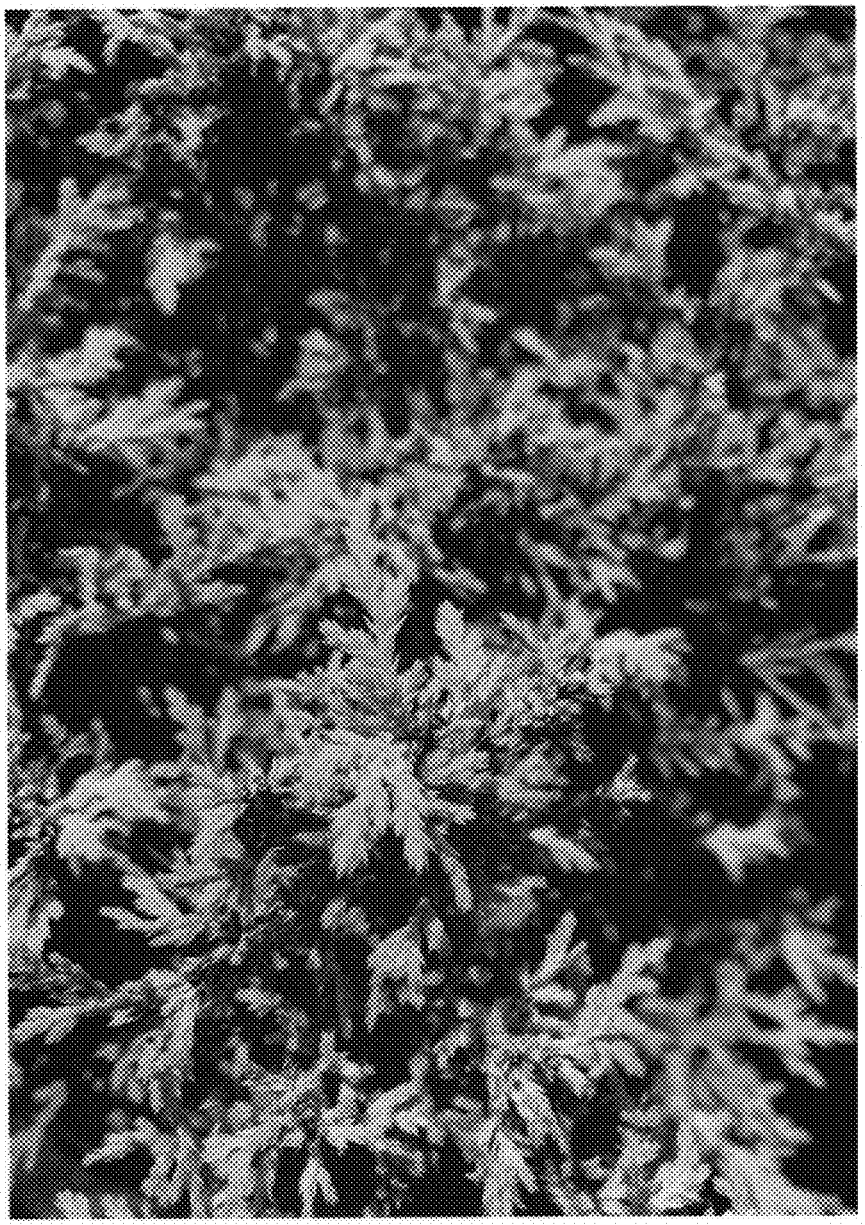

FIG. 2 illustrates a close-up view of the foliage. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'FARROWCGMS' plants grown in a poly greenhouse during Summer, in Grand Haven, Mich. USA. The growing temperature ranged from 18° C. to 27° C. during the day and from 5° C. to 10° C. during the night. General light conditions are natural sunlight. Measurements and numerical values represent averages of typical plant types.

Botanical classification: *Chamaecyparis pisifera* 'FARROWCGMS'.

PROPAGATION

Typical method: Softwood cuttings.

Time to initiate rooting: 120 days at approximately 10° C.

Time to produce a rooted young plant: 180 days at approximately 10° C. to 13° C.

Root description: Fine and fleshy roots present. Moderately well branched. Colored light brown, not accurately measured with an R.H.S. chart.

PLANT

Age of plant described: 2 to 3 years.

Container size of plant described: 3 gallon.

Growth habit: Evergreen tree, slightly mounding in juvenility, then growing upright.

Height: 87 cm.

Plant spread: 79 cm.

Typical growth rate: Rapid. Average growth per year ranges between 1.5 to 2.5 feet, depending upon environmental conditions.

Branching characteristics: Upright and outwards.

Angle: 5 to 85°.

Quantity of lateral branches: 14.

Length of lateral branches: 46 cm.

Diameter of lateral branches: 1 cm.

Lateral branch shape: Round.

Stem strength: Strong.

Stem color: Greyed-Orange 177 C.

Internode length: Average 2 cm.

Trunk bark:

*Color*.—Near RHS Greyed-Orange 177A.

*Texture*.—Rough, scaly.

FOLIAGE

General description: Overlapping scales.

Leaf:

*Arrangement*.—Overlapping scales.

*Shape of blade*.—Scale-like.

*Apex*.—Acute.

*Base*.—Cuneate.

*Margin*.—Entire.

*Texture of top surface*.—Smooth, moderately glossy.

*Texture of bottom surface*.—Smooth, moderately glossy.

*Foliage color*.—Varies with light exposure along branch. Foliage on lower section of branch receives less light. Top of branch leaves, upper: Majority of surface Yellow 7A, small lower section near Yellow-Green N144C. Top of branch leaves, under: Majority of surface Yellow 7A, lower section near Yellow-Green N144C. Middle branch leaves, upper: Mostly Yellow-Green N144C, with some Yellow-Green 7A. Middle branch leaves, under: Yellow-Green 143C with some Yellow Green 145A at the tips. Lower, interior branch leaves, upper: Green 141B. Lower, interior branch leaves, under: Green 141B.

*Venation*.—Not observable.

*Fragrance*.—Not observed.

FLOWER

Flowering not observed.

OTHER CHARACTERISTICS

Disease and pest resistance: Neither resistance nor susceptibility observed.

Drought tolerance: No tolerance for drought.

Temperature tolerance: −32 to 36 degree C.

What is claimed is:

1. A new and distinct cultivar of *Chamaecyparis* plant named 'FARROWCGMS' as herein illustrated and described.

* * * * *